(12) United States Patent
Ho et al.

(10) Patent No.: US 10,585,027 B2
(45) Date of Patent: Mar. 10, 2020

(54) PARTICLE SENSING DEVICE AND ELECTRONIC APPARATUS HAVING THE SAME

(71) Applicant: Winbond Electronics Corp., Taichung (TW)

(72) Inventors: Yu-Hsuan Ho, Taichung (TW); Yi-Der Wu, Taichung (TW)

(73) Assignee: Winbond Electronics Corp., Taichung (TW)

( * ) Notice: Subject to any disclaimer, the term of this patent is extended or adjusted under 35 U.S.C. 154(b) by 0 days.

(21) Appl. No.: 15/473,645

(22) Filed: Mar. 30, 2017

(65) Prior Publication Data
US 2017/0299489 A1   Oct. 19, 2017

(30) Foreign Application Priority Data

Apr. 15, 2016 (CN) .......................... 2016 1 0235833

(51) Int. Cl.
*G01N 15/06* (2006.01)
*G01N 27/22* (2006.01)
(Continued)

(52) U.S. Cl.
CPC ..... *G01N 15/0656* (2013.01); *G01N 15/0606* (2013.01); *G01N 15/1031* (2013.01);
(Continued)

(58) Field of Classification Search
CPC ........................ G01N 15/0656; G01N 15/1031
See application file for complete search history.

(56) References Cited

U.S. PATENT DOCUMENTS 7,579,823 B1   8/2009 Ayliffe
9,116,249 B1 *  8/2015 Claus ........................ G01T 1/16
(Continued)

FOREIGN PATENT DOCUMENTS

CN      104792845       7/2015
CN      205092897       3/2016
(Continued)

OTHER PUBLICATIONS

"Office Action of Taiwan Counterpart Application," dated May 12, 2017, p. 1-p. 4, in which the listed references were cited.
(Continued)

*Primary Examiner* — Patrick Assouad
*Assistant Examiner* — Feba Pothen
(74) *Attorney, Agent, or Firm* — JCIPRNET

(57) ABSTRACT

A particle sensing device, including a substrate and at least one particle sensing element, is provided. The substrate has a groove, and a through hole is disposed at a bottom of the groove. The through hole penetrates a bottom of the substrate. The particle sensing element is disposed in the substrate. The particle sensing element may include a first electrode pair and a second electrode pair. Two first sub-electrodes of the first electrode pair are disposed nearby two sides of the groove, respectively. And, a first distance is provided between the two first sub-electrodes. Two second sub-electrodes of the second electrode pair are disposed nearby two sides of the groove, respectively. And, a second distance is provided between the two second sub-electrodes. The first distance is smaller than the second distance.

18 Claims, 8 Drawing Sheets

(51) Int. Cl.
*G01N 15/10* (2006.01)
*G01N 33/00* (2006.01)
*G01N 15/00* (2006.01)

(52) U.S. Cl.
CPC ......... G01N 27/22 (2013.01); G01N 33/0036 (2013.01); *G01N 2015/0046* (2013.01)

(56) References Cited

U.S. PATENT DOCUMENTS

| | | | |
|---|---|---|---|
| 9,316,576 B2* | 4/2016 | Hongo | G01N 15/12 |
| 2007/0117243 A1* | 5/2007 | Sharma | B81C 1/00063 |
| | | | 438/49 |
| 2009/0149227 A1* | 6/2009 | Yamaguchi | H04M 1/0249 |
| | | | 455/575.3 |
| 2012/0064567 A1* | 3/2012 | Stakenborg | B03C 5/005 |
| | | | 435/39 |
| 2014/0305191 A1* | 10/2014 | Schmid | G01N 29/022 |
| | | | 73/24.03 |

FOREIGN PATENT DOCUMENTS

| | | | |
|---|---|---|---|
| KR | 1399005 B1 * | 5/2014 | |
| TW | I404924 | 8/2013 | |

OTHER PUBLICATIONS

"Office Action of China Counterpart Application," dated May 20, 2019, p. 1-p. 21.

* cited by examiner

PARTICLE SENSING DEVICE AND ELECTRONIC APPARATUS HAVING THE SAME

CROSS-REFERENCE TO RELATED APPLICATION

This application claims the priority benefit of China application serial no. 201610235833.5, filed on Apr. 15, 2016. The entirety of the above-mentioned patent application is hereby incorporated by reference herein and made a part of this specification.

BACKGROUND

Technical Field

The disclosure relates to a particle sensing device, and more particularly, relates to a particle sensing device and an electronic apparatus having the particle sensing device, which are capable of sensing the particulate matter (PM) in the air.

Description of Related Art

In recent years, owing to the rising awareness of environment protection, people have gradually paid more attention to air quality in the living environment. The particulate matter refers to a mixture of particles and droplets, and serves as a pollutant standard index. Because fine particles with diameter less than or equal to 10 micrometer (μm) can enter the lung through the nose and the throat, particulate matter 2.5 and particulate matter 10 are now defined as the major indicators affecting human health. Particulate matter 2.5 (PM 2.5) refers to fine particles with aerodynamic diameter less than or equal to 2.5 micrometer, and particulate matter 10 (PM 10) refers to inhalable coarse particles with aerodynamic diameter less than or equal to 10 micrometer. Because particle sizes of the particulate matters are very small, the particulate matters can stay in the atmosphere for a very long time and travel for a very long distance. As a result, the particulate matters can lead to serious deterioration on air quality and visibility.

The particulate matters can absorb a large amount of toxic and hazardous substances. Apart from that, research also indicates that PM 10 can easily attach onto the respiratory system and the organs in human body, and PM 2.5 can directly penetrate the alveolus into the vessels and circulate with blood circulation around the entire body to cause allergies, asthma, emphysema, lung cancer, cardiovascular diseases, liver cancer, blood diseases, etc. In other words, the particulate matters can severely affect human health.

In order to detect the particulate matter in the atmosphere, a capacitive-type particle sensor has been introduced in related art, as shown by FIG. 1. FIG. 1 is a schematic diagram of a capacitive-type particle sensor in conventional art. Referring to FIG. 1, a capacitive-type particle sensor 100, including a first interdigitated electrode 110 and a second interdigitated electrode 120, is provided. The first interdigitated electrode 110 includes a plurality of first electrode fingers 112 and a first connection electrode 114 connected to the first electrode fingers 112. A first connection port 114a is provided at one end of the first interdigitated electrode 110 and configured to input/output signals.

The second interdigitated electrode 120 includes a plurality of second electrode fingers 122 and a second connection electrode 124 connected to the second electrode fingers 122. A second connection port 124a is provided at one end of the second interdigitated electrode 120 and configured to input/output signals.

After entering a gap between the first electrode fingers 112 and the second electrode fingers 122, the particulate matters change a dielectric constant between the first electrode fingers 112 and the second electrode fingers 122 thereby correspondingly changing a capacitance therein. In this way, the particulate matters may be measured.

However, the capacitive-type particle sensor 100 in conventional art is extremely sensitive to ambient temperature, moisture in the air, etc. In other words, the capacitance measured by the capacitive-type particle sensor 100 (which, theoretically, should only include influences of the particulate matters) usually includes influences of temperature and moisture as well; thus, it is additionally required to perform temperature and moisture calibrations for the measured capacitance. Besides, due to a poor recognition capability for the particle sizes, the capacitive-type particle sensor 100 in conventional art can only measure increase or decrease in a particle amount, relatively.

SUMMARY

The disclosure provides a particle sensing device with a recognition capability for sizes of the particulate matters, which can sense the particulate matters satisfactorily and can be easily integrated to various electronic apparatuses.

The disclosure also provides an electronic apparatus having aforesaid particle sensing device and capable of easily sensing the particulate matter in the environment.

The particle sensing device of the disclosure includes a substrate and at least one particle sensing element. The substrate has a groove, and a through hole is disposed at a bottom of the groove. The through hole penetrates a bottom of the substrate. The particle sensing element is disposed in the substrate. Herein, the particle sensing element may include a first electrode pair and a second electrode pair. Two first sub-electrodes of the first electrode pair are disposed nearby two sides of the groove, respectively. A first distance is provided between the two first sub-electrodes. Two second sub-electrodes of the second electrode pair are disposed nearby two sides of the groove, respectively. A second distance is provided between the two second sub-electrodes. Herein, the first distance is smaller than the second distance, and the first electrode pair is closer to the through hole than the second electrode pair.

The electronic apparatus of the disclosure includes a body and the above mentioned particle sensing device. The particle sensing device is electrically coupled to the body.

Based on the above, by disposing multiple electrode pairs in 3D space with use of the three dimensional stacking electrode design, the particle sizes may be determined and a density of the particulate matter in the air may also be measured. Further, a miniaturized particle sensing device with the recognition capability for the particle sizes may be realized. In addition, the particle sensing device may be easily manufactured and integrated to most of portable electronic apparatuses.

To make the above features and advantages of the disclosure more comprehensible, several embodiments accompanied with drawings are described in detail as follows.

DESCRIPTION OF THE EMBODIMENTS

Figure 1:
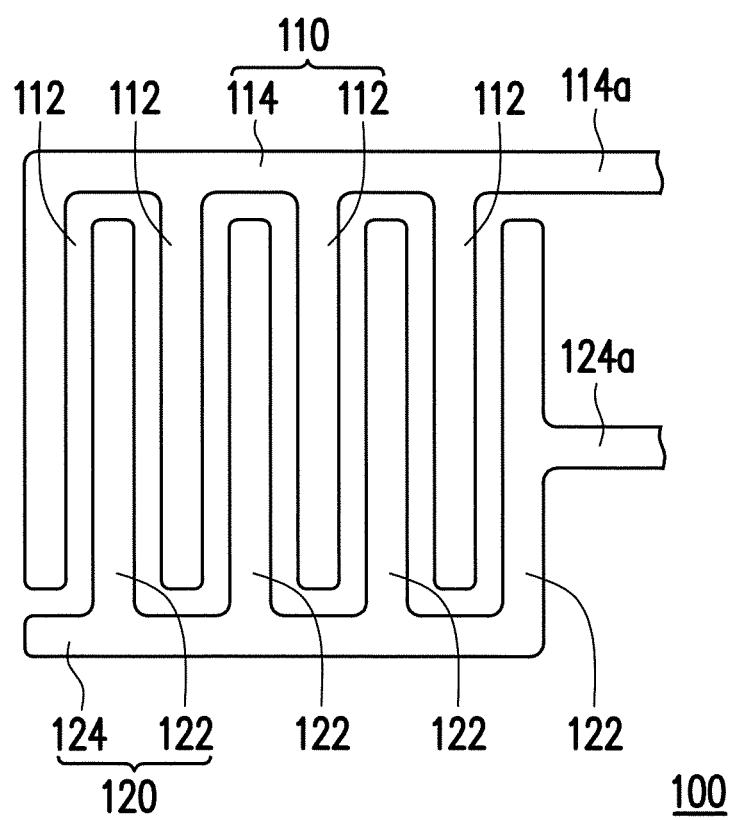
FIG. 1 is a schematic view of a capacitive-type particle sensor in conventional art.
Figure 2A:
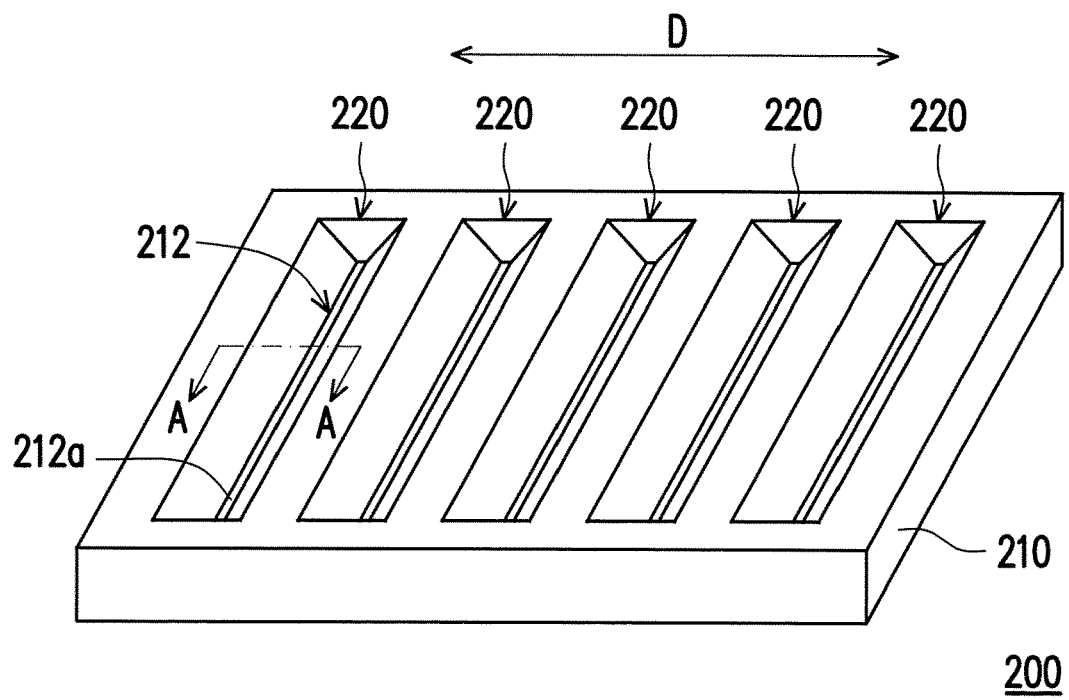
FIG. 2A is a three-dimensional view of a particle sensing device according to an embodiment of the disclosure.
Figure 2B:
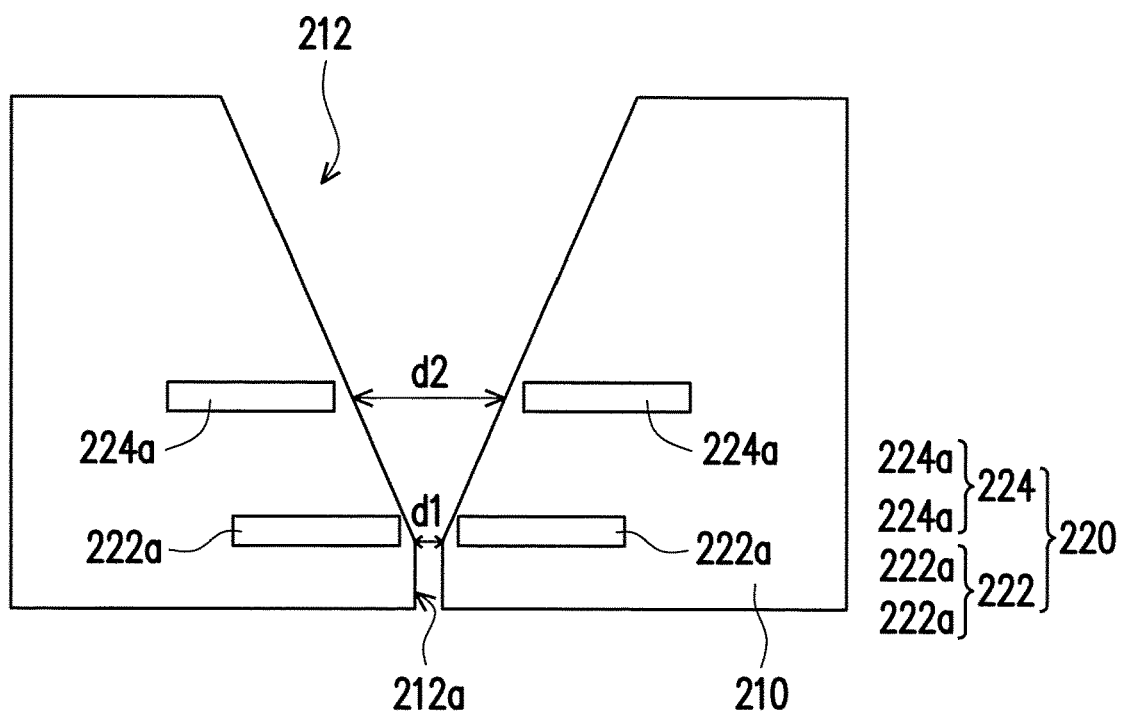
FIG. 2B is a cross-sectional view of the particle sensing device of FIG. 2A taken along a sectional line A-A.

FIG. 2A is a three-dimensional view of a particle sensing device according to an embodiment of the disclosure. FIG. 2B is a cross-sectional view of the particle sensing device of FIG. 2A taken along a sectional line A-A. FIG. 2A and FIG. 2B illustrate the condition before particulate matters P enter the particle sensing device. Please referring to FIG. 2A and FIG. 2B, a particle sensing device 200 may include a substrate 210 and at least one particle sensing element 220. The substrate 210 has at least one groove 212. In this embodiment, particle sensing elements 220 and grooves 212 are provided. A through hole 212a is disposed at a bottom of each groove 212. The through hole 212a penetrates a bottom of the substrate 210.

The particle sensing element 220 is disposed in the substrate 210. Herein, the particle sensing element 220 may include a first electrode pair 222 and a second electrode pair 224. Two first sub-electrodes 222a of the first electrode pair 222 are disposed opposite to each other and nearby two sides of the groove 212, respectively. A first distance d1 is provided between the two first sub-electrodes 222a. The first distance d1 is a width of the groove 212 corresponding to a position of the first electrode pair 222. Two second sub-electrodes 224a of the second electrode pair 224 are disposed opposite to each other and nearby two sides of the groove 212, respectively. A second distance d2 is provided between the two second sub-electrodes 224a. Herein, the first distance d1 is smaller than the second distance d2. The first electrode pair 222 is closer to the through hole 212a than the second electrode pair 224. The second distance d2 is a width of the groove 212 corresponding to a position of the second electrode pair 224.

In the particle sensing device 200 shown by FIG. 2A and FIG. 2B, the first electrode pair 222 and the second electrode pair 224 may be manufactured by using a three dimensional stacking (printing) technology. In this way, the first electrode pair 222 may be used to measure the particulate matter with a size close to the first distance d1, and the second electrode pair 224 may be used to measure the particulate matter with a size close to the second distance d2. Thus, the particulate matters of two different sizes may then be recognized.

Further, by disposing the first electrode pair 222 and the second electrode pair 224 inside and not being exposed outside the substrate 210, the first electrode pair 222 and the second electrode pair 224 may be protected from damages caused by external temperature variation (high temperature) or moisture erosion, and may be prevented from oxidation or scratches to thereby significantly improve a device reliability of the particle sensing device 200. Moreover, a sensing reliability of the particle sensing device 200 is relatively higher since the influences of the external temperature variation or moisture are reduced. As such, the subsequent steps of calibrating the data of measured capacitance (i.e., calculating steps of subtracting the influences of the external temperature variation or moisture on the capacitance) may be omitted.

Figure 2C:
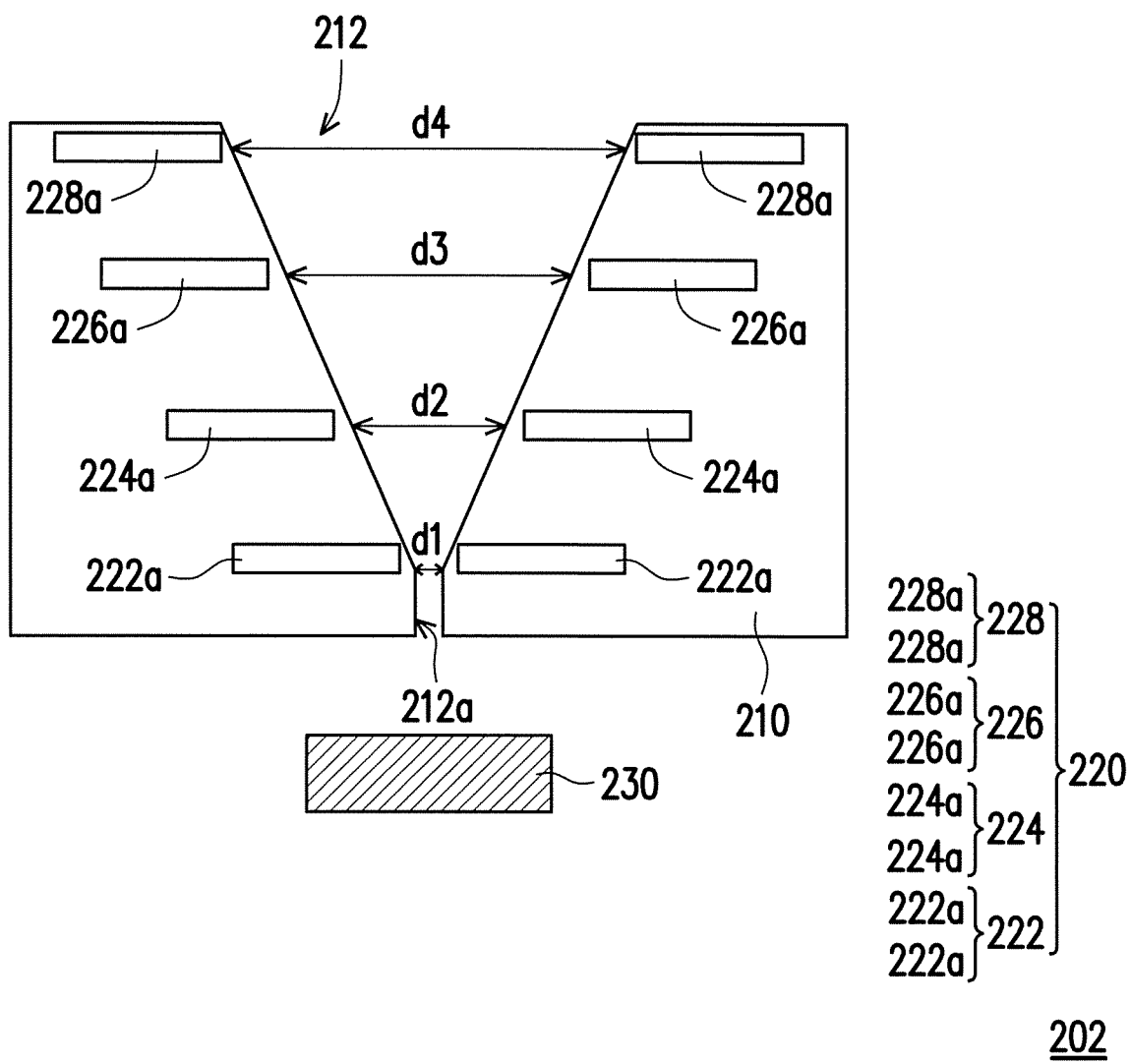
FIG. 2C is a cross-sectional view of a particle sensing device according to another embodiment of the disclosure.

FIG. 2C is a cross-sectional view of a particle sensing device according to another embodiment of the disclosure. Elements in FIG. 2C identical to those provided in FIG. 2B are represented by the same reference numbers, and their descriptions are not repeated hereinafter. Please referring to FIG. 2C, a particle sensing device 202 may further include a third electrode pair 226 disposed in the substrate 210. Two third sub-electrodes 226a of the third electrode pair 226 are disposed opposite to each other and nearby two sides of the groove 212, respectively. A third distance d3 is provided between the two third sub-electrodes 226a. Herein, the second distance d2 is smaller than the third distance d3. The second electrode pair 224 is closer to the through hole 212a than the third electrode pair 226. The third distance d3 is a width of the groove 212 corresponding to a position of the third electrode pair 226. Furthermore, the particle sensing device 202 may also include a fourth electrode pair 228 disposed in the substrate 210. Two fourth sub-electrodes 228a of the fourth electrode pair 228 are disposed opposite to each other and nearby two sides of the groove 212, respectively. A fourth distance d4 is provided between the two fourth sub-electrodes 228a. Herein, the third distance d3 is smaller than the fourth distance d4. The third electrode pair 226 is closer to the through hole 212a than the fourth electrode pair 228. The fourth distance d4 is a width of the groove 212 corresponding to a position of the fourth electrode pair 228.

In view of FIG. 2C, the particle sensing device 202 includes the first electrode pair 222 to the fourth electrode pair 228. Accordingly, the first electrode pair 222 may be used to measure the particulate matter with a size close to the first distance d1; the second electrode pair 224 may be used to measure the particulate matter with a size close to the second distance d2; the third electrode pair 226 may be used to measure the particulate matter with a size close to the third distance d3; and the fourth electrode pair 228 may be used to the measure particulate matter with a size close to the fourth distance d4. Thus, the particulate matters of four different sizes may then be recognized. In the embodiments of the disclosure, a quantity of the electrode pairs is merely an example rather than limitation to the scope of the disclosure. Based on design requirements, person with ordinary skill in the related technical field can appropriately set the quantity of the electrode pairs and the distance between two sub-electrodes of the electrode pair in order to measure the particulate matters of different sizes.

In an embodiment of the disclosure, the first distance d1 is 2.5 micrometer, the second distance d2 is 10 micrometer, the third distance d3 is 50 micrometer, and the fourth distance d4 is 100 micrometer. As such, the particulate matters in different size ranges may then be measured.

Further, referring back to FIG. 2C, the particle sensing device 202 may also include an air pump 230, which is disposed under the through hole 212a. The air pump 230 may be used to extract the air from the groove 212 via the through hole 212a while measuring the particulate matters. By doing so, a speed for the particulate matters to fall between any one of the first electrode pair 222 to the fourth electrode pair 228 may be accelerated. In addition, the air pump 230 may also be used to clean the groove 212. That is to say, the particulate matters may be exhausted from the groove 212 after inducing the air into the groove 212 via the through hole 212a. As such, a self-cleaning function may then be achieved.

Referring back to FIG. 2A, the particle sensing elements 220 are provided to be arranged along a set direction D of the substrate 210. By disposing multiple particle sensing elements 220, a large area sensing operation may be performed on the particulate matters, so as to improve a sensitivity for sensing the particulate matters.

Figure 3:
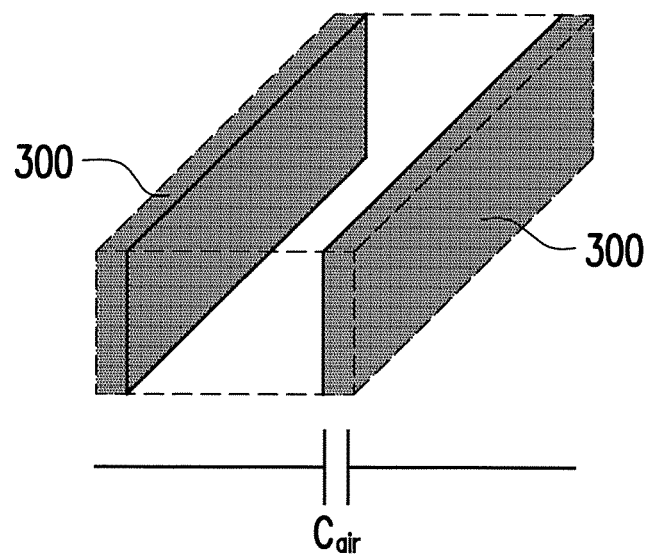
FIG. 3 is a schematic view of a capacitance measured before the particulate matter enters between the electrode pair.
Figure 4:
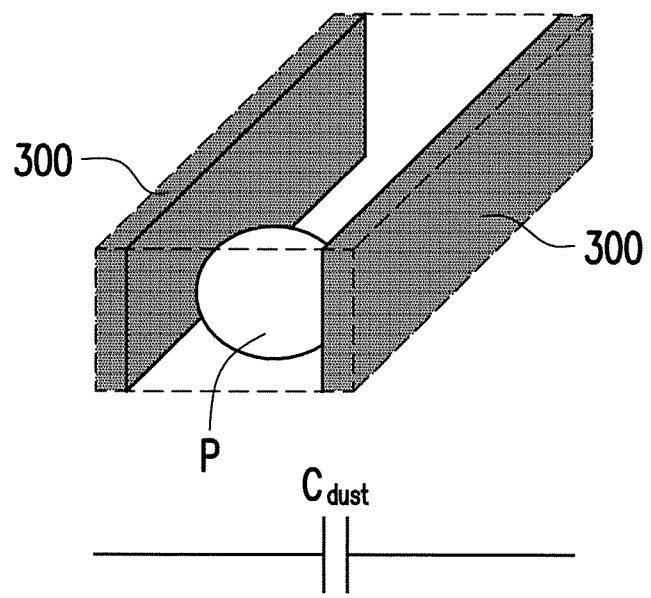
FIG. 4 is a schematic view of a capacitance measured after the particulate matter enters between the electrode pair.

FIG. 3 is a schematic view of a capacitance measured before the particulate matter enters between the electrode pair. FIG. 4 is a schematic view of a capacitance measured after the particulate matter enters between the electrode pair. Referring to FIG. 3, before any particulate matter enters between a pair of sub-electrodes 300, a capacitance $C_{air}$ in a clean air condition may be measured. Further, referring to FIG. 4, after the particulate matter P enters between the pair of sub-electrodes 300, a capacitance $C_{dust}$ may be measured. It is set herein that, a density of the particulate matter P is $D_{particles}$, a filling factor in capacitor of the particulate matter P is $\gamma_{dust}$, and a dielectric constant of the particulate matter P is $\varepsilon_{r,\,dust}$. Aforesaid parameters can satisfy Equation (1) and Equation (2) below.

$$C_{dust} = [\gamma_{dust} \cdot \varepsilon_{r,dust} + (1 - \gamma_{dust})] \cdot C_{air} \quad (1)$$

Through Equation (1) above, Equation (2) below may be derived.

$$\gamma_{dust} = \frac{C_{dust}/C_{air} - 1}{\varepsilon_{r,dust} - 1} \propto D_{particles} \quad (2)$$

In other words, with the measured capacitances $C_{air}$ and $C_{dust}$ and the known dielectric constant $\varepsilon_{r,\,dust}$ of the particulate matter P, the filling factor in capacitor $\gamma_{dust}$ may be calculated, where the filling factor in capacitor $\gamma_{dust}$ is proportional to the density $D_{particles}$ of the particulate matter P. As a result, the density of the particulate matter P may be measured by using the particle sensing devices 200 and 202 provided in the embodiments of the disclosure.

Figure 5:
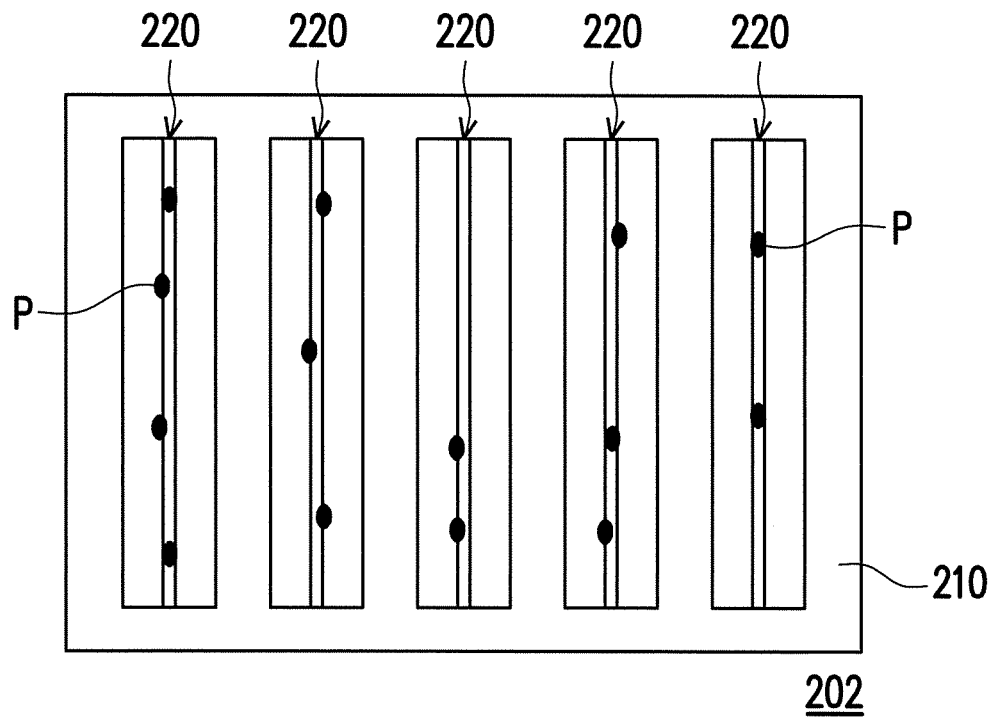
FIG. 5 is a top view of a particle sensing device according to an embodiment of the disclosure, which illustrates the condition where the particulate matters have entered the particle sensing device.
Figure 6:
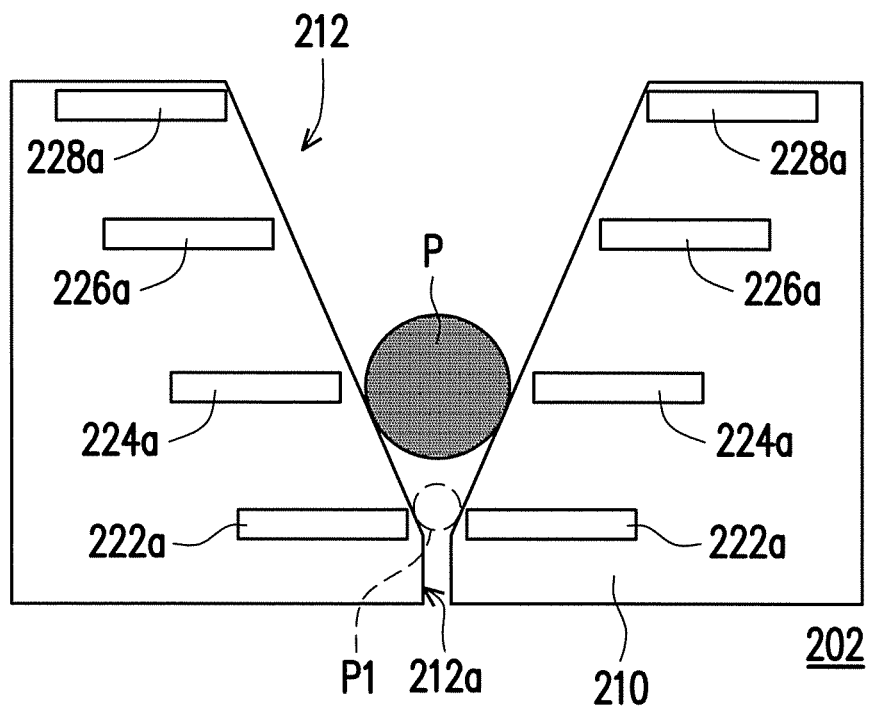
FIG. 6 is a cross-sectional view of the particle sensing device of FIG. 5.

FIG. 5 is a top view of a particle sensing device according to an embodiment of the disclosure, which illustrates the condition where the particulate matters have entered the particle sensing device. FIG. 6 is a cross-sectional view of the particle sensing device of FIG. 5.

Referring to FIG. 5 and FIG. 6, when the particulate matter P enters the groove 212 and falls on the position corresponding to the second sub-electrodes 224a, it can be observed that a capacitance between the two second sub-electrodes 224a changes significantly. Accordingly, it can be determined that a particle size of the particulate matter P is close to the size of the second distance d2 (e.g., 10 micrometer). Further, in view of the contents of Equation (1) and Equation (2) as described in FIG. 3 and FIG. 4, the density of the particulate matter P in the air may be learned.

As another condition, when a particulate matter P1 (as shown by dash lines in FIG. 8) enters the groove 212 and falls on the position corresponding to the first sub-electrodes 222a, it can be observed that a capacitance between the two first sub-electrodes 222a changes significantly. Accordingly, it can be determined that a particle size of the particulate matter P1 is close to the size of the first distance d1 (e.g., 2.5 micrometer). Similarly, in view of the contents of Equation (1) and Equation (2) as described in FIG. 3 and FIG. 4, the density of the particulate matter P1 in the air may be learned.

It should be noted that, the measurement of the two first sub-electrodes 222a for the particulate matter P1 and the measurement of the two second sub-electrodes 224a for the particulate matter P may be performed at the same time. In other words, the particle sensing device 202 can simultaneously sense the particulate matters P1 (PM 2.5) and P (PM 10), which are of two different sizes. Because of the first electrode pair 222 to the fourth electrode pair 228 being included, the particle sensing device 202 is capable of simultaneously measuring the particulate matters of four different sizes.

In the foregoing embodiments, sectional shapes of the grooves 212 in the particle sensing devices 200 and 202 is V-shaped. However, the sectional shape of the groove 212 may also be U-shaped in a particle sensing device 204 shown by FIG. 7 or stair shaped in a particle sensing device 206 shown by FIG. 8.

The shape deign for the groove 212 may be used to improve a filtering precision for the particulate matters of different sizes. For instance, by providing steps between electrode pairs in the stair shaped groove 212 shown by FIG. 8, the particulate matters P1, P, and P2 may be satisfactorily engaged between the two first sub-electrodes 222a, the two second sub-electrodes 224a, and the two third sub-electrodes 226a, respectively. Therefore, the filtering precision for the particulate matters of different sizes may then be improved. The particle sensing device 206 is capable of satisfactorily sensing the particulate matters P, P1 and P2 simultaneously to obtain three measured signals which are not interfering with one another. Naturally, although FIG. 8 merely illustrates the condition regarding the three particulate matters P, P1 and P2, the measurements for the particulate matters of four different sizes may be performed at the same time if the particulate matter measurable by the two fourth sub-electrodes 228a also exists.

Figure 9:
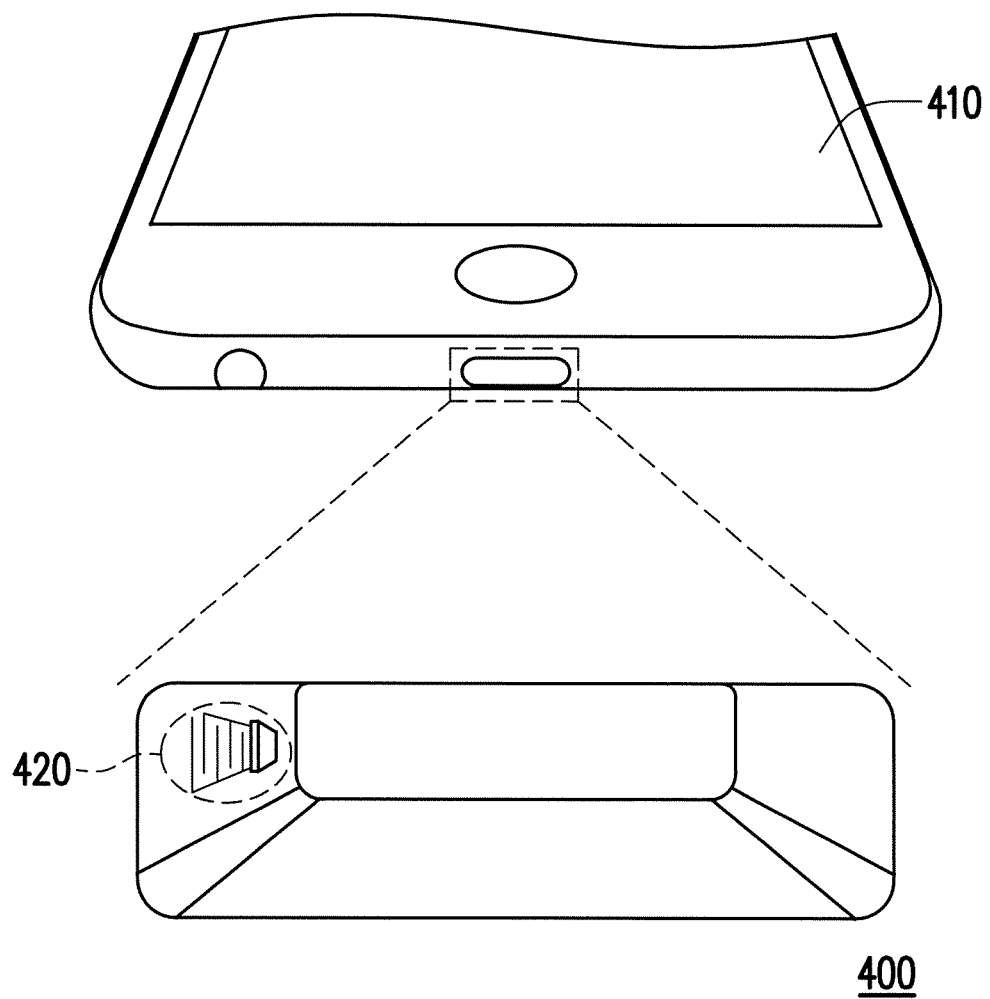
FIG. 9 is a schematic view of an electronic apparatus according to an embodiment of the disclosure.

FIG. 9 is a schematic view of an electronic apparatus according to an embodiment of the disclosure. Referring to FIG. 9, an electronic apparatus 400 includes a body 410 and a particle sensing device 420. The particle sensing device 420 is electrically coupled to the body 410.

Figure 7:
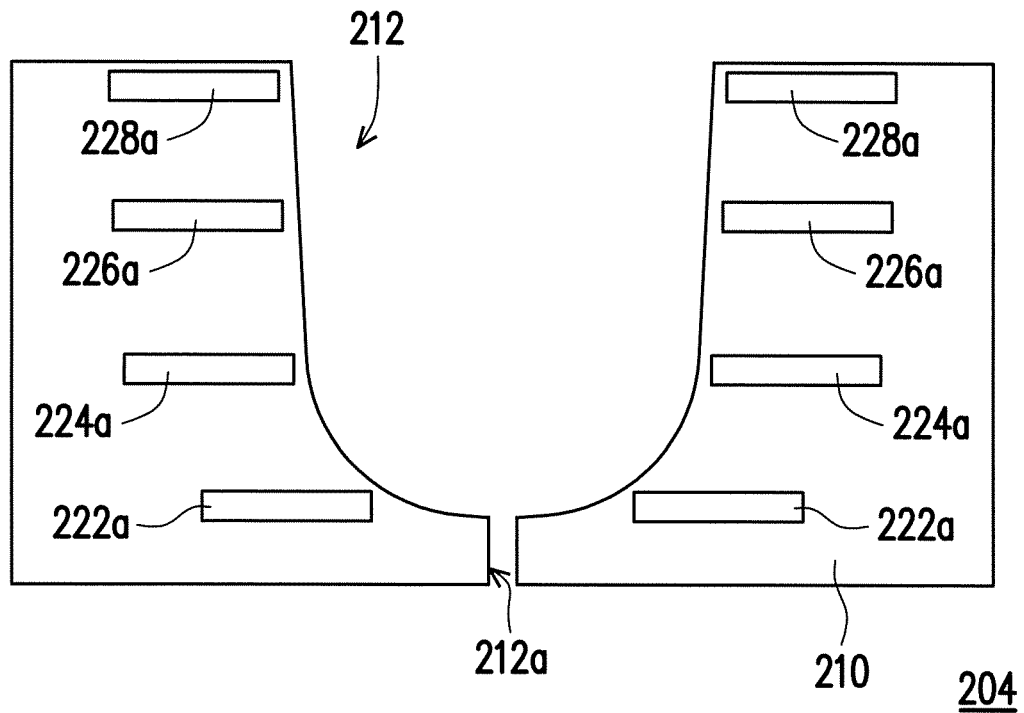
FIG. 7 is a cross-sectional view of a particle sensing device according to yet another embodiment of the disclosure.
Figure 8:
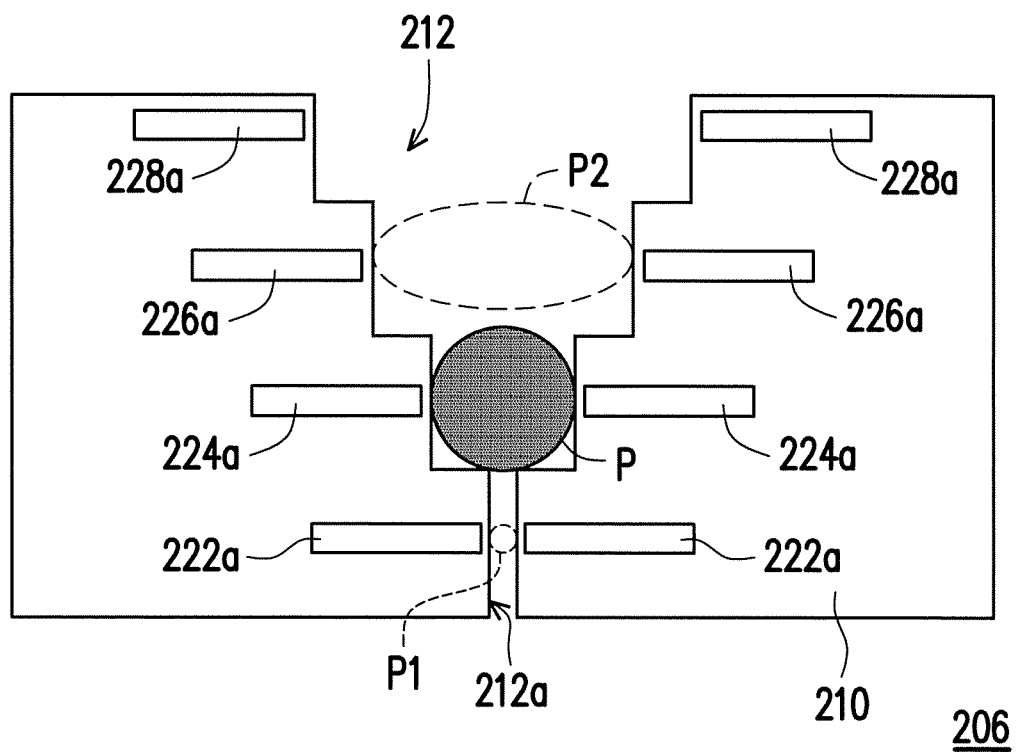
FIG. 8 is a cross-sectional view of a particle sensing device according to still another embodiment of the disclosure.

The particle sensing device 420 may adopt any one of the particle sensing device 200 shown by FIG. 2A and FIG. 2B, the particle sensing device 202 shown by FIG. 2C, the particle sensing device 204 shown by FIG. 7 and the particle sensing device 206 shown by FIG. 8, and the descriptions of the above are not repeated hereinafter. In the electronic apparatus 400 in FIG. 9, the particle sensing device 420 is embedded in the body 410 of the electronic apparatus 400. For example, as shown by a partial enlarged diagram in FIG. 9, the particle sensing device 420 is disposed on a sidewall of a universal serial bus (USB) port of the body 410.

The electronic apparatus 400 may be any portable electronic apparatus, such as a smart phone, a tablet computer, a notebook computer, a virtual reality display, a wearable electronic apparatus (e.g., a smart bracelet, a smart glasses, etc.) and the like. Specifically, the particle sensing device 420 provided in the present embodiment of the disclosure may be easily integrated to the electronic apparatuses, such that people can use the same to easily sense ambient particulate matters in order to obtain density data of the particulate matters for related applications.

For example, in the application of the wearable electronic apparatus, when the user wearing the smart bracelet conducts any activity in one specific environment, the particle sensing device 420 of the present embodiment of the disclosure integrated to the smart bracelet can sense the density of the particulate matter in the specific environment in real time through a capacitance-type sensing operation and report a sensing result back to the user. After discovering that the density of the particulate matter in the specific environment is overly high, the user can immediately reacts by, for example, leaving the specific environment or putting on a protective mask, and so on.

As another example, in the application of the virtual reality display, when the user wearing the virtual reality display enters one specific environment, the particle sensing device 420 of the present embodiment of the disclosure integrated to the virtual reality display can sense the density of the particulate matter in the specific environment and converts the density data into a visible image. Accordingly, the user is able to view a virtual appearance of the particulate matter in the specific environment (e.g., dense particulate matters may be viewed when the density is high; whereas a natural environment may be displayed when the density is low).

Figure 10:
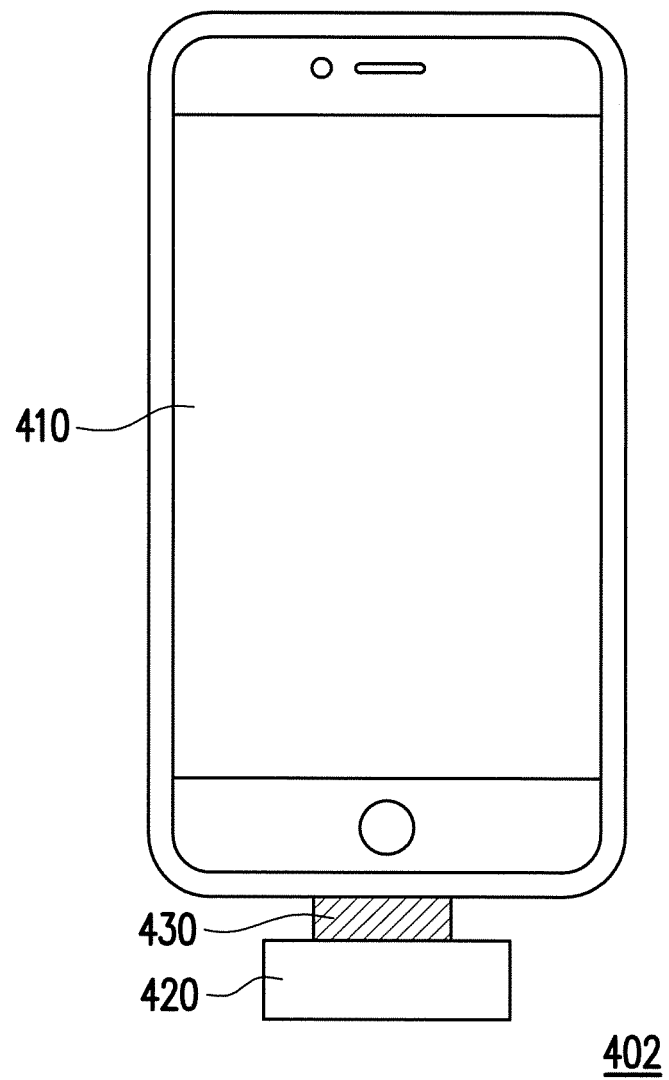
FIG. 10 is a schematic view of an electronic apparatus according to another embodiment of the disclosure.

FIG. 10 is a schematic view of an electronic apparatus according to another embodiment of the disclosure. In an embodiment of the disclosure, an electronic apparatus 402 may further include an electrical connection element 430, and the particle sensing device 420 is externally connected on the body 410 of the electronic apparatus 402 through the electrical connection element 430. The electrical connection element 430 may adopt a USB connection or other suitable electronically connection methods, which are not particularly limited by the disclosure.

In other words, the electronic apparatus 402 shown by FIG. 10 can use particle sensing device 420 through an external connection; the particle sensing device 420 may be detached when the use of the particle sensing device 420 is not required. With the external connection design, a flexibility and a degree of freedom for using the particle sensing device 420 in cooperation with the body 410 may be improved dramatically.

The particle sensing devices 200 to 206 and 420 are capable of using a plurality of electrode pairs (the first to the fourth electrode pairs 222 to 228) to sense the particulate matters of different sizes (i.e., the recognition capability for the sizes of particulate matters). Further, the particle sensing devices 200 to 206 and 400 may be easily integrated to any portable electronic apparatus. Accordingly, the user is able to use the portable electronic apparatus (e.g., the smart phone) to sense the density of particulate matter in the air at any time. The sensed data may also be applied to the technical field related to IoT (Internet of Things) and Big data. The interpretation of the data can create huge contribution in the field of atmospheric science, environment science, epidemiology, environmental protection and medicine, etc.

In summary, the particle sensing device and the electronic apparatus of the disclosure at least includes the following advantages. First of all, by disposing the multiple electrode pairs in 3D space, the particle size may be determined (the recognition capability for the particle sizes) and the density of the particulate matters in the air may also be measured. Also, the electrode pairs are disposed in the substrate. Therefore, the influences of external temperature variation and moisture are prevented so the device reliability and the sensing reliability of the particle sensing device may be improved. Furthermore, the particle sensing device may be easily manufactured, easily miniaturized, and integrated to most of portable electronic apparatuses.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A particle sensing device, comprising:
   a substrate, having a groove including a through hole penetrating a bottom of the substrate; and
   at least one particle sensing element disposed in the substrate, so as to be not exposed outside of the substrate, comprising:
   a first electrode pair having two first sub-electrodes being disposed nearby two sides of the groove, respectively, and a first distance being provided between the two first sub-electrodes; and
   a second electrode pair having two second sub-electrodes being disposed nearby two sides of the groove, respectively, a second distance being provided between the two second sub-electrodes, wherein the first distance is smaller than the second distance, the first electrode pair is closer to the bottom of the substrate than the second electrode pair, and by measuring a change of a first capacitance between the two first sub-electrodes and a change of a second capacitance between the two second sub-electrodes, particles having different sizes corresponding to the first distance and the second distance are available to be detected.

2. The particle sensing device of claim 1, further comprising:
   a third electrode pair, disposed in the substrate, two third sub-electrodes of the third electrode pair being disposed nearby two sides of the groove, respectively, a third distance being provided between the two third sub-electrodes, wherein the second distance is smaller than the third distance, and the second electrode pair is closer to the through hole than the third electrode pair.

3. The particle sensing device of claim 2, further comprising:
   a fourth electrode pair, disposed in the substrate, two fourth sub-electrodes of the fourth electrode pair being disposed nearby two sides of the groove, respectively, a fourth distance being provided between the two fourth sub-electrodes, wherein the third distance is smaller than the fourth distance, and the third electrode pair is closer to the through hole than the fourth electrode pair.

4. The particle sensing device of claim 3, wherein
   the first distance is 2.5 micrometer, the second distance is 10 micrometer, the third distance is 50 micrometer, and the fourth distance is 100 micrometer.

5. The particle sensing device of claim 1, further comprising:
   an air pump, disposed under the through hole.

6. The particle sensing device of claim 1, wherein a plurality of the particle sensing elements are arranged along a set direction of the substrate.

7. The particle sensing device of claim 1, wherein
a sectional shape of the grove is V-shaped, U-shaped or stair shaped.

8. The particle sensing device of claim 1, wherein the particle sensing element is manufactured by a three dimensional stacking technology.

9. An electronic apparatus, comprising:
a body; and
a particle sensing device, electrically coupled to the body, the particle sensing device comprising:
a substrate, having a groove including a through hole penetrating a bottom of the substrate; and
at least one particle sensing element disposed in the substrate, so as to be not exposed outside of the substrate, comprising:
a first electrode pair having two first sub-electrodes being disposed nearby two sides of the groove, respectively, and a first distance being provided between the two first sub-electrodes; and
a second electrode pair having two second sub-electrodes being disposed nearby two sides of the groove, respectively, a second distance being provided between the two second sub-electrodes, wherein the first distance is smaller than the second distance, the first electrode pair is closer to the bottom of the substrate than the second electrode pair, and by measuring a change of a first capacitance between the two first sub-electrodes and a change of a second capacitance between the two second sub-electrodes, particles having different sizes corresponding to the first distance and the second distance are available to be detected.

10. The electronic apparatus of claim 9, further comprising:
a third electrode pair, disposed in the substrate, two third sub-electrodes of the third electrode pair being disposed nearby two sides of the groove, respectively, a third distance being provided between the two third sub-electrodes, wherein the second distance is smaller than the third distance, and the second electrode pair is closer to the through hole than the third electrode pair.

11. The electronic apparatus of claim 10, further comprising:
a fourth electrode pair, disposed in the substrate, two fourth sub-electrodes of the fourth electrode pair being disposed nearby two sides of the groove, respectively, a fourth distance being provided between the two fourth sub-electrodes, wherein the third distance is smaller than the fourth distance, and the third electrode pair is closer to the through hole than the fourth electrode pair.

12. The electronic apparatus of claim 11, wherein
the first distance is 2.5 micrometer, the second distance is 10 micrometer, the third distance is 50 micrometer, and the fourth distance is 100 micrometer.

13. The electronic apparatus of claim 9, further comprising:
an air pump, disposed under the through hole.

14. The electronic apparatus of claim 9, wherein a plurality of the particle sensing elements are arranged along a set direction of the substrate.

15. The electronic apparatus of claim 9, wherein
a sectional shape of the grove is V-shaped, U-shaped or stair shaped.

16. The electronic apparatus of claim 9, wherein
the particle sensing device is embedded in the body of the electronic apparatus.

17. The electronic apparatus of claim 9, further comprising:
an electrical connection element, and
the particle sensing device being externally connected on the body of the electronic apparatus through the electrical connection element.

18. The electronic apparatus of claim 9, wherein the particle sensing element is manufactured by a three dimensional stacking technology.

* * * * *